United States Patent [19]

Piccardi et al.

[11] 4,299,837
[45] Nov. 10, 1981

[54] ANTHELMINTIC BENZIMIDAZOLE-CARBAMATES

[75] Inventors: Paolo Piccardi, Milan; Giovanni Confalonieri, Monza; Lino Da Col; Pier G. Ramella, both of Novara, all of Italy

[73] Assignee: Montedison S.p.A., Milan, Italy

[21] Appl. No.: 156,109

[22] Filed: Jun. 3, 1980

Related U.S. Application Data

[63] Continuation-in-part of Ser. No. 100,522, Dec. 5, 1979, abandoned.

[51] Int. Cl.³ .................. C07D 235/32; A61K 31/415
[52] U.S. Cl. .................................. 424/273 B; 548/306
[58] Field of Search .................... 548/306; 424/273 B

[56] References Cited

U.S. PATENT DOCUMENTS

| | | | |
|---|---|---|---|
| 3,010,968 | 11/1961 | Loux | 548/306 |
| 3,480,642 | 11/1969 | Stedman | 548/306 |
| 3,915,986 | 10/1975 | Gyurik et al. | 548/306 |
| 4,002,640 | 1/1977 | Beard et al. | 548/306 |
| 4,145,431 | 3/1979 | Haujwitz et al. | 548/306 |
| 4,156,006 | 5/1979 | Haujwitz et al. | 548/306 |
| 4,182,893 | 1/1980 | Piccardi et al. | 548/306 |

FOREIGN PATENT DOCUMENTS

| | | |
|---|---|---|
| 2816694 | 10/1978 | Fed. Rep. of Germany . |
| 2843008 | 4/1979 | Fed. Rep. of Germany . |
| 2052988 | 4/1971 | France . |
| 1114069 | 5/1968 | United Kingdom . |
| 1360180 | 7/1974 | United Kingdom . |
| 1376713 | 12/1974 | United Kingdom . |
| 1455728 | 11/1976 | United Kingdom . |
| 1456497 | 11/1976 | United Kingdom . |

*Primary Examiner*—Henry R. Jiles
*Assistant Examiner*—Natalie Harkaway

[57] ABSTRACT

Benzimidazole-carbamates endowed wth anthelmintic activity, and substituted in position 5(6) by a diene chain bound to the position 5(6) by an oxygen or sulphur atom optionally oxidized, are described.

The processes for their preparation, the intermediates thereof, and their use as anthelmintics are described too.

44 Claims, No Drawings

ANTHELMINTIC BENZIMIDAZOLE-CARBAMATES

This invention relates to benzimidazole-carbamates endowed with anthelmintic activity; more particularly it relates to new benzimidazole-carbamates substituted in position 5(6) by a diene chain bound to position 5(6) by an atom of oxygen or of sulphur optionally oxidized, and the use thereof as anthelminthes.

Benzimidazole-derivatives exist in tautomeric forms such as

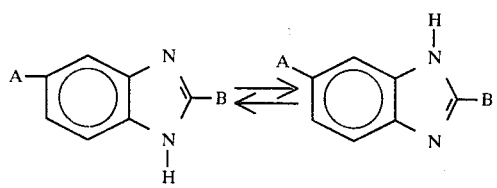

For nomenclature convention the substituent A which is in position 5 in a tautomeric form, assumes position 6 in the other tautomeric form.

So a benzimidazole-derivatives having a substituent in the position corresponding to substituent A, is generally defined as "5(6)-substituted".

Several benzimidazole-carbamates variously substituted in position 5(6), as well as their anthelmintic action are known (see for example German patent application Nos. 2,029,637 and 2,164,690; French Pat. Nos. 1,556,824 and 2,052,988; U.S. Pat. Nos. 3,010,968, 3,915,986 and 4,002,640).

Anthelmintic benzimidazole-carbamates have been described also in German patent application Nos. 2,816,694 and 2,843,308 in the name of the applicants.

Many benzimidazole-carbamates substituted in position 5(6) have been put on the market, such as for example Albendazole, Oxibendazole and Parbendazole produced by Smith Kline Co.; Phenbendazole produced by Hoechst; Oxphendazole produced by Syntex; Cambendazole and Thiabendazole produced by Merck, and Mebendazole produced by Janssen.

We have now found new benzimidazole-carbamates, which constitute the object of the present invention, substituted in position 5(6), having the formula:

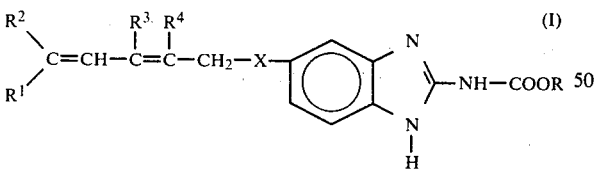

wherein:
R = alkyl $C_1$–$C_4$;
$R^1$ and $R^2$ (like or unlike each other) = H, halogen, methyl optionally substituted by one or more halogen atoms;
$R^3$ and $R^4$ (like or unlike each other) = H, Cl, $CH_3$;
X = O, S, SO, $SO_2$.

The compounds of general formula I are endowed with a high anthelmintic activity and a wide action spectrum being active against both gastrointestinal and broncho-pulmonary parasites and against hepatic parasites of domestic and breeding animals.

The synthesis of the compounds of formula (I) is carried out according to simple steps, as results from the following scheme (wherein R, $R^1$, $R^2$, $R^3$ and $R^4$ have the same meanings indicated in formula (I); Z and Z' = Cl, Br; $R^5$ = H, $CH_3CO$):

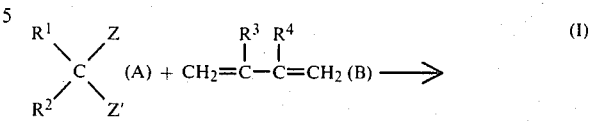

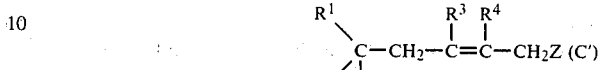

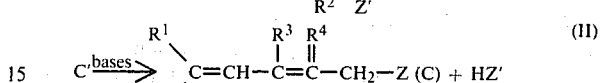

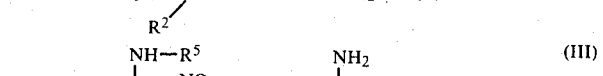

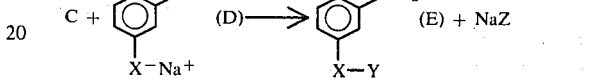

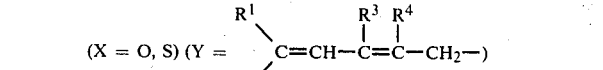

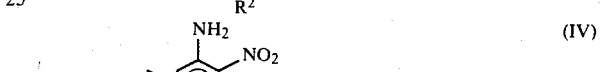

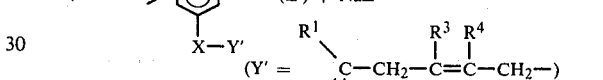

The first passage of the scheme of reaction for obtaining the compounds of formula (I) (reaction I), i.e. the reaction between a compound of formula

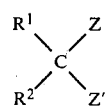

[wherein $R^1$ and $R^2$ have the meanings indicated in general formula (I), and Z and Z' (like or unlike each other) are Cl, Br] and a diene of the type

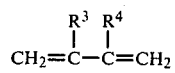

[wherein $R^3$ and $R^4$ have the same meanings specified in general formula (I)], is conducted by radical intermediates in the presence of suitable catalysts such as Redox-transfer systems, as for example copper salts and amines, as described by B. M. Asscher et al. [J. Chem.

Soc. page 1887 (1963)], or in the presence of ruthenium complexes, as more recently described by H. Matsumoto et al. [Chemistry Letters, page 115 (1978)] for the reaction between CCl4[(A), $R^1\!=\!R^2\!=\!Z\!=\!Z'\!=\!Cl$] an isoprene

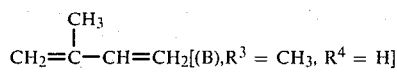
$[(B), R^3 = CH_3, R^4 = H]$ in the presence of dichloro-tris-triphenyl-phosphine-ruthenium ($Ru^{II}[P(C_6H_5)_3]_3Cl_2$).

It is important to point out that reaction I, both when conducted in the presence of Redox-transfer systems, and when conducted in the presence of ruthenium complexes, is not region-selective, wherefore when in compound B substituent $R^3$ is different from $R^4$, also mixtures of positional isomers, besides mixtures of cis-trans isomers due the presence of the double bond, are obtained.

For example, starting from CCl4 and isoprene, mixtures of the following compounds are obtained:

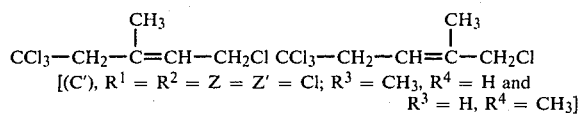
$[(C'), R^1 = R^2 = Z = Z' = Cl; R^3 = CH_3, R^4 = H$ and $R^3 = H, R^4 = CH_3]$ Generally, the mixture of the positional isomers is separable into the individual isomers by fractional distillation.

The compounds of formula (C) or (C') are then reacted with the sodium salt of 2-nitro-4-hydroxy-aniline (sodium phenate) [(D), X=O, $R^5$=H] or of 2-nitro-4-mercapto-aniline (sodium mercaptate) [(D), X=S, $R^5$=H] according to reactions III and IV.

In some cases it is preferable to protect the amino group of compounds (D) by acetylation starting then from the corresponding N-acetyl-anilines [(D), $R^5$=CH_3CO].

The acetyl group then can be easily removed by hydrolysis at the more convenient step of the process.

In this manner, nitro-aniline of formula (E) or (E') are obtained. The latter, when treated with bases, undergoes a dehydrohalogenation on its side chain in position 4 with respect to the amino group (X-Y'), so providing the nitro-aniline indicated by letter (E) (reaction V).

Nitro-aniline (E) is then reduced, for example, with sodium hydrosulphite ($Na_2S_2O_4$), so obtaining phenylenediamine (F) (reaction VI).

Phenylenediamine F is then reacted with 1,3-bis-alkoxycarbonyl-S-methyl-isothiourea, so obtaining benzimidazole-carbamates of general formula (I), in which X=O or X=S (reaction VII).

By reacting phenylenediamine F with 1,3-bis-methoxycarbonyl-S-methyl-isothiourea compounds of formula I in which R is methyl are obtained.

In a similar manner by reacting phenylenediamine F with 1,3-bis-ethoxycarbonyl-S-methyl-isothiourea or 1,3-bis-propoxycarbonyl-S-methyl-isothiourea or 1,3-bis-butoxycarbonyl-S-methyl-isothiourea, benzimidazole-carbamates of formula I are prepared in which R is either ethyl, propyl or butyl.

Finally, from the benzimidazole-carbamates of formula (I), in which X=S, it is possible to obtain, by oxidation with peracids, the compounds of formula (I), in which X=SO or $SO_2$ (reaction VIII).

Reaction VIII is conveniently carried out by dissolving the benzimidazole-carbamate of formula I (in which X=S) in an inert solvent (or in a mixture of inert solvents) and by adding at a temperature of from $-30°$ C. to room temperature, a peracid such as peracetic acid, perbenzoic acid or 3-chloro-perbenzoic acid.

When it is desired to convert the thio group to its corresponding sulphinyl group, equimolecular quantities of peracids are used. While when it is desired to convert the thio group to its corresponding sulphonyl group, or to convert the sulphinyl group to its corresponding sulphonyl group, an excess of peracid is used.

As examples of compounds of formula:

the following may be cited: $CHBr_3$, $CHCl_3$, $CBr_4$, $CCl_4$, $CH_3$—$CCl_3$, $CH_3$—$CHCl_2$, $CF_3$—$CHBr_2$, $CF_3$—$CHClBr$, $CF_3$—$CFBr_2$, $CF_3$—$CCl_3$, $CF_2Cl$—$CFCl_2$, $CF_3$—$CBr_3$, $CF_2Br_2$, $CF_2Cl$—$CCl_3$, $CF_3$—$CBr_2$—$CF_3$ $CH_3$—$CClBr$—$CH_3$.

As examples of compounds of formula

the following may be cited:

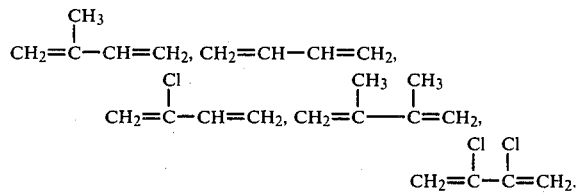

Some of the compounds indicated by the letters C and C' on scheme 1 are known compounds such as the aforementioned adduct of carbon tetrachloride and isoprene or 1-bromo-exa-2,4-diene(sorbyl bromide) of formula $CH_3$—$CH$=$CH$—$CH$=$CH$—$CH_2Br$ or 5-chloro-1,3-pentadiene of the formula

described in Russian Pat. No. 472,926 [Chemical Abstract 83, 78559×(1975)].

However, in the course of the studies carried out on the synthesis of the benzimidazole-carbamates of general formula (I), it has been noticed that many of the intermediates indicated by the letters C and C' on scheme 1 are compounds previously unknown, wherefore the compounds having the general formulae given hereinbelow are a further object of this invention:

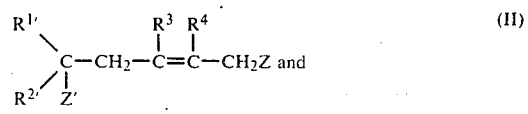

-continued $$\begin{array}{c} R^{1'} \\ \diagdown \\ \diagup \\ R^{2'} \end{array} C=CH-\overset{R^3}{\underset{|}{C}}=\overset{R^4}{\underset{|}{C}}-CH_2Z \qquad (III)$$

wherein:
$R^{1'}$ = F, methyl substituted by one or more halogen atoms,
$R^{2'}$ = halogen, methyl substituted by one or more halogen atoms,
Z and Z' (like or unlike each other) = Cl, Br,
$R^3$ and $R^4$ (like or unlike each other) = H, $CH_3$.

Some of the compounds of general formulae II and III can be prepared also by other methods.

For example, compounds in which $R^3$ = H and $R^4$ = $CH_3$ can be prepared by reacting the corresponding compounds in which Z = H with N-halo imides (N-bromo-succinimide etc.) in the presence of radical reaction promoters.

As already mentioned hereinabove, the compounds of general formula (I) are endowed with a high anthelmintic activity and a wide action range, these characteristics permitting to successfully fight infestations in mammals and birds, for example in the domestic and breeding animals.

Compounds of formula I are active against gastrointestinal parasites such as Ostertagia spp., Trichostrongylus spp., Strongyloides spp., Trichuris spp., Oesophagostum spp., Chabertia spp., Nematodirus spp., Moniezia spp., Cooperia spp., Haemonchus spp., against broncho-pulmonary parasites such as Dictyocaulus spp., and against hepatic parasites such as Fasciola spp..

The latter characteristic can be difficult to find in the known anthelminthes. The wide field of action of the compounds of general formula (I) represents an important characteristic as the administration of same to infested animals causes a simultaneous liberation of the animal from gastrointestinal, hepatic and broncho-pulmonary parasites. Furthermore, compounds of formula I have been found to be active against other nematode parasites of the order of Filarioidea, including *Brugia pahangi* and *Dirofilaria immitis*.

The activity of compounds according to the present invention was determined in experiments conducted on naturally infested sheep or, in the case of Fasciola, on artificially infested sheep. The animals were divided into two groups, one of which was treated with one dose of the product being tested (orally) while the other untreated group was used as check. During 48–72 hours after treatment with the compound being tested, the excrements of the animals were collected in order to determine the number of parasites or of eggs; successively, the animals were killed to determine the reduction of the infestation in comparison with the check.

For veterinary use, the administration of the compounds of this invention to the animals to be treated can be effected according to the usual veterinary techniques for the anthelmintic treatment, namely orally in the form of boluses, tablets, suspensions, etc., by injections in the form of an injectable liquid or by absorption through the skin (spot on).

It is important to notice that the anthelmintic compounds object of the present invention are endowed, unlike known anthelminthes, with a good solubility (about 20% by weight) in N-methyl-2-pyrrolidone, an injectable liquid employed in the veterinary technique.

The amounts to be given depend on various factors, among which important are the weight of the animal to be treated, the nature and the severity of the infestation. Suitable doses are at the discretion of the veterinary physician but may be within the range of 0.5 to 100 mg of the compound of formula I per kg body weight of the host, preferably 1 to 10 mg/Kg.

Little animals need amounts of a few milligrams of anthelmintic compound, while great animals, such as cattle, sheep, etc., may need amounts of the order of grams per subject.

In practice, the active compound is usually formulated with a vehicle agent (carrier) of veterinary use, or directly in the food for the animal. The active compound may be mixed or dispersed in one of the components of the food, or utilized in the form of boluses, tablets easily ingestable or capsules, drenching, suspensions, powders, pastes, salt licks, block licks, granules, pellets feed premixes. The carrier may be also a pharmaceutic diluent or excipient of the type generally employed in the formulation of medicines; easily available products are, for example, the following: maize starch, terra alba, lactose, saccharose, calcium phosphate, gelatin, stearic acid, magnesium stearate, dextrin, agar, pectins, vegetable oils, injectable liquid carriers such as propylene glycol, N-methyl-2-pyrrolidone, and so on.

If desired other active ingredients such as other anthelmintics, food and mineral supplements may be included in the formulation.

The way of administering may vary remarkably and depends on the specific requirements.

With respect to anthelmintic activity, preferred compounds are thio-derivatives (X=S) and sulphinyl derivatives (X=SO). Some of the samples tested for anthelmintic activity were mixtures of positional isomers ($R^3$ different from $R^4$).

However the anthelmintic activity of samples of different composition is practically non-affected by the relative positional isomers ratio (see example 21).

The following examples are given to better illustrate the invention.

EXAMPLE 1

Preparation of 1,5,5-trichloro-3-methylhex-2-ene(A) and of 1,5,5-trichloro-2-methylhex-2-ene (B)

[Mixture No. 1]

In a "Pfaudler" type autoclave of 2.5 l capacity the following compounds were introduced under vacuum:

- 1,1,1-trichloroethane ($CH_3$—$CCl_3$) 1200 ml
- isoprene ($CH_2$=$\overset{CH_3}{\underset{|}{C}}$—CH=$CH_2$) 500 ml
- Ruthenium-tris-triphenylphosphine-dichloride $Ru^{II}[(C_6H_5)_3P]_3Cl_2$ 7.5 g.

The content of the autoclave was then stirred and heated up to 90° C. At this temperature an exothermic reaction began and the temperature raised to 130° C.

The reaction was continued for 2 and half hours keeping the temperature between 120° and 130° C., then the autoclave was left to cool at room temperature. The reaction mixture was then concentrated by evaporation at reduced pressure (20 mmHg, 40° C.).

The residue of about 800 g was diluted with 1200 ml of petroleum ether. The ruthenium complex precipitated and was quantitatively recovered by filtration. The filtrate was again concentrated by evaporation and the residue was distilled under reduced pressure. The fraction boiling between 82° and 85° C. at 5 mmHg was gathered (690 g).

Nuclear Magnetic Resonance (NMR) analysis revealed that the collected fraction was a mixture of compounds (A) and (B) in a ratio of about 85:15

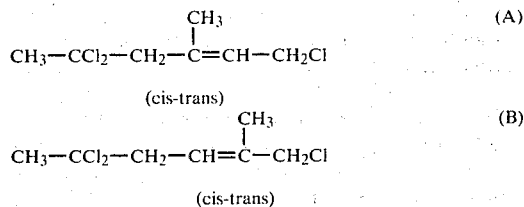

(cis-trans)

EXAMPLE 2

By operating analogously with what is described in Example 1, the compounds or mixtures of compounds reported on the following Table 1, were prepared.

EXAMPLE 3

Preparation of 1,5,5,5-tetrachloro-3-methyl-pent-2-ene (A) and of 1,5,5,5-tetrachloro-2-methyl-pent-2-ene (B) by redox-transfer catalyst $CuCl_2.2H_2O$ (2 g) was introduced into an enamelled autoclave of 2.5 l capacity.

The air was eliminated from the autoclave and, under vacuum, the following compounds were introduced:
  a solution of n.butyl-amine (n.$C_4H_9$-$NH_2$) (3.65 g) in acetonitrile ($CH_3CN$) (300 ml)
  a mixture of carbon tetrachloride ($CCl_4$) (600 ml) and isoprene (300 ml)
  carbon tetrachloride (200 ml).

The autoclave was then heated at 90°–130° C. in three hours keeping the internal pressure at 7–8 atm by adding small amounts of isoprene from a small cylinder.

Then the autoclave was left to cool at room temperature, and was opened. The content of the autoclave was distilled at reduced pressure (about 20 mmHg) in order to eliminate the volatile components from the reaction mixture (isoprene, $CCl_4$ and $CH_3CN$). The residue was

TABLE 1

Compounds of formula $$\begin{array}{c} R^1 \\ \diagdown \\ \phantom{R^2}C-CH_2-C=C-CH_2Z \\ \diagup \phantom{C} | \\ R^2 \phantom{C} Z' \end{array}$$ with $R^3, R^4$ on the central carbons

| Compound n° (or Mixture No.) | Formula[a] | | Starting Products[b] | Boiling Point of collected fraction (°C./mmHg) | Positional isomers ratio[c] (A/B) |
|---|---|---|---|---|---|
| 1[d] | $CH_3-CCl_2-CH_2-C(CH_3)=CH-CH_2Cl$ | (A) | $CH-CCl_3$ + I. | 82–85/5 | 85:15 |
|  | $CH_3-CCl_2-CH_2-CH=C(CH_3)-CH_2Cl$ | (B) |  |  |  |
| 2 | $CF_3-CBr_2-CH_2-C(CH_3)=CH-CH_2Br$ | (A) | $CF_3-CBr_3$ + I. | 72/2 | 3:2 |
|  | $CF_3-CBr_2-CH_2-CH=C(CH_3)-CH_2Br$ | (B) |  |  |  |
| 3 | $CF_3-CFBr-CH_2-C(CH_3)=CH-CH_2Br$ | (A) | $CF_3-CFBr_2$ + I. | 62/5 | 1:1 |
|  | $CF_3-CFBr-CH_2-CH=C(CH_3)-CH_2Br$ | (B) |  |  |  |
| 4 | $CF_2Cl-CCl_2-CH_2-C(CH_3)=CH-CH_2Cl$ | (A) | $CF_2Cl-CCl_3$ + I. | 90–95/7 | 1:1 |
|  | $CF_2Cl-CCl_2-CH_2-CH=C(CH_3)-CH_2Cl$ | (B) |  |  |  |
| 5 | $CF_2Br-CH_2-C(CH_3)=CH-CH_2Br$ | (A) | $CF_2Br_2$ + I. | 90/3 | 7:3 |
|  | $CF_2Br-CH_2-CH=C(CH_3)-CH_2Br$ | (B) |  |  |  |
| 6 | $CF_2Br-CH_2-CH=CH-CH_2Br$[e] |  | $CF_2Br_2$ + B. |  |  |
| 7 | $CF_3-CCl_2-CH_2-C(CH_3)=CH-CH_2Cl$ | (A) | $CF_3-CCl_3$ + I. | 60/2 | 3:2 |
|  | $CF_3-CCl_2-CH_2-CH=C(CH_3)-CH_2Cl$ | (B) |  |  |  |
| 8 | $CF_3-CHCl-CH_2-C(CH_3)=CH-CH_2Cl$ | (A) | $CF_3-CHClBr$ + I. | 56/1 | 5:2 |
|  | $CF_3-CHCl-CH_2-CH=C(CH_3)-CH_2Cl$ | (B) |  |  |  |
| 9 | $CHCl_2-CH_2-C(CH_3)=CH-CH_2Cl$ | (A) | $CHCl_3$ + I. | —[f] | 2:1 |
|  | $CHCl_2-CH_2-CH=C(CH_3)-CH_2Cl$ | (B) |  |  |  |
| 10 | $CHBr_2-CH_2-CH=CH-CH_2Br$[g] |  | $CHBr_3$ + B. | 140/0.5 |  |
| 11 | $CHBr_2-CH_2-C(CH_3)=CH-CH_2Br$ | (A) | $CHBr_3$ + I. | 115/3 | 5:2 |
|  | $CHBr_2-CH_2-CH=C(CH_3)-CH_2Br$ | (B) |  |  |  |
| 12 | $CCl_3-CH_2-CH=CH-CH_2Cl$[g] |  | $CCl_4$ + B. | 69/1.5 |  |
| 13 | $CBr_3-CH_2-CH=CH-CH_2Br$[g] |  | $CBr_4$ + B. | 135/1 |  |
| 14 | $CH_3-CCl_2-CH_2-CH=CH-CH_2Cl$[g] |  | $CH_3-CCl_3$ + B. | 67/5 |  |
| 15 | $CF_3-CBr_2-CH_2-CH=CH-CH_2Br$[g] |  | $CF_3-CBr_3$ + B. | 75/3 |  |
| 16[h] | $CCl_3-CH_2-C(CH_3)=CH-CH_2Cl$ | (A) | $CCl_4$ + I. | 61–63/1 | 9:1 |
|  | $CCl_3-CH_2-CH=C(CH_3)-CH_2Cl$ | (B) |  |  |  |
| 17 | $CBr_3-CH_2-C(CH_3)=CH-CH_2Br$ | (A) | $CBr_4$ + I. | 140–145/1 | 60:40 |
|  | $CBr_3-CH_2-CH=C(CH_3)-CH_2Br$ | (B) |  |  |  |

Notes to Table 1
[a]Mixture of cis and trans isomers

[b]I = isoprene ($CH_2=C(CH_3)-CH=CH_2$), B = butadiene ($CH_2=CH-CH=CH_2$)
[c]Approximate ratio determined by NMR spectroscopy
[d]The preparation of Mixture No. 1 is described in Example 1
[e]Spectroscopic data of compound No. 6
  NMR (solvent $CDCl_3$, internal standard TMS) δ, ppm:
  3.1 (d.t., 2H, $J_{H,H}$ = 5.66 Hz, $J_{H,F}$ = 12.8 Hz)
  3.8–4 (m, 2H)
  5.3–6.3 (m, 2H)
  (d.t. = doublet of triplet, m = multiplet, J = coupling constant)
[f]Mixture No. 9 was isolated as pure (GLC) as residue after distillation from the reaction crude of unreacted $CHCl_3$ and isoprene.
[g]NMR spectroscopic data consistent with the assigned structure.
[h]An analogous preparation has been described by J. Tanaka et al. [Nippon Kagaku Zasshi 90, 803 (1969)] (100% of isomer A).

distilled under high vacuum collecting all the distilled material in a single fraction which was then re-distilled collecting the fraction (570 g) boiling at 65° C. (1.3 mmHg). NMR analysis revealed that the collected fraction was a mixture of compounds A and B (97% pure by GLC) in a ratio of about 70:30. An analogous preparation has been described by P. Piccardi et al. [Agric. and Food Chem. 25/5, 1073 (1977)]

EXAMPLE 4

Preparation of 1,1,5-trichloro-3-methyl-penta-1,3-diene (A) and of 1,1,5-trichloro-4-methyl-penta-1,3-diene (B)

[Reaction II]

200 g of the mixture of compounds, prepared as described in Example 3, were dissolved in benzene (240 ml). The solution was added to a solution of NaOH (162 g) in H$_2$O (210 g) in the presence of tetrabutylammonium iodide (n.C$_4$H$_9$)$_4$N$^+$ $^-$ (1.2 g). The reaction mixture was maintained under intense stirring at 25°–30° C. for 5 hours.

The organic layer was separated and the aqueous layer, after neutralization with hydrochloric acid, was extracted with diethyl-ether (2×100 ml). The organic phases were reunited and anhydrified on anhydrous Na$_2$SO$_4$. The solvents were evaporated under vacuum, the residue was distilled and the fraction boiling at 50°–52° C. (0.7 mmHg) was collected. NMR analysis revealed that the collected fraction was a mixture of compounds A and B in a ratio of about 60:40 (pure at 93% by GLC).

EXAMPLE 5

Preparation of 1,1-dichloro-4-methyl-5-bromo-penta-1,3-diene

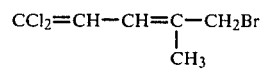  (A)

By a procedure analogous to the one described in Example 1, CCl$_4$ (243 ml) was additioned to isopentene CH$_2$=CH—CH(CH$_3$)$_2$ (66 g) in the presence of Ru$^{II}$[(C$_6$H$_5$)$_3$P]$_3$Cl$_2$ (1.8 g) obtaining 1,1,1,3-tetrachloro-4-methyl-pentane (45 g)

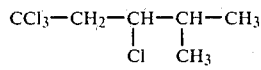

The product thus obtained was dehydrohalogenated by treatment with (C$_2$H$_5$)$_3$N (41.4 g) in DMF at reflux temperature for 10 hours. The reaction mixture was then poured in H$_2$O (100 ml) and extracted by ethyl ether.

The organic solution was distilled and the fraction boiling at 44° C. (4 mmHg) consisting of 1,1-dichloro-4-methyl-penta-1,3-diene was collected (NMR consistent with the assigned structure

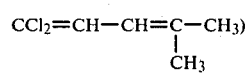

16.3 g of the product thus obtained were dissolved in CCl$_4$ (50 ml) and additioned with N-bromosuccinimide (19.3 g) in the presence of azobis-isobutyronitrile (100 mg). The reaction mixture was refluxed for 8 hours. The succinimide was filtered, the solvent was eliminated under vacuum and the residue was distilled.

The fraction boiling at 93°–96° C./2 mmHg (14.6 g) was collected. NMR data are consistent with the structure assigned to compound A.

EXAMPLE 6

By operating as described in Example 5 and starting from 2,5-dimethyl-hexa-2,4-diene the compound 1-bromo-2,5-dimethyl-hexa-2,4-diene was obtained (NMR consistent with the assigned structure)

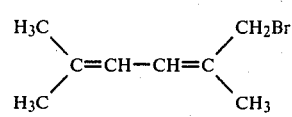

EXAMPLE 7

By operating analogously to what is described in Example 4, the compounds (or mixtures of compounds) reported in the following Table 2, were prepared.

TABLE 2

Compounds of formula:

$$\begin{array}{c}R^1\\ \phantom{R^1}\diagdown\\ \phantom{R^1R^2}C=CH-\overset{R^3}{\underset{|}{C}}=\overset{R^4}{\underset{|}{C}}-CH_2Z\\ \phantom{R^1}\diagup\\ R^2\end{array}$$

| Compound No. (Mixture No.) | Formula$^{(a)}$ | | Starting Product(s) (see Table 1) | Boiling Point of collected fraction (°C./mmHg) | Positional Isomers ratio$^{(b)}$ (A/B) |
|---|---|---|---|---|---|
| 18$^{(c)}$ | CCl$_2$=CH—C(CH$_3$)=CH—CH$_2$Cl | (A) | Mixture of Example 3 | 50–52/0.7 | 60:40 |
|  | CCl$_2$=CH—CH=C(CH$_3$)—CH$_2$Cl | (B) |  |  |  |
| 19 | CCl$_2$=CH—CH=CH—CH$_2$Cl |  | 12 | 63/15 |  |
| 20 | CH$_3$—C(Cl)=CH—C(CH$_3$)=CH—CH$_2$Cl | (A) | 1 | 42–45/0.2 | 78:22 |
|  | CH$_3$—C(Cl)=CH—CH=C(CH$_3$)—CH$_2$Cl | (B) |  |  |  |
| 21 | CF$_3$—CF=CH—C(CH$_3$)=CH—CH$_2$Br | (A) | 3 | —$^{(d)}$ | 65:35 |
|  | CF$_3$—CF=CH—CH=C(CH$_3$)—CH$_2$Br | (B) |  |  |  |
| 22 | CF$_3$—C(Br)=CH—C(CH$_3$)=CH—CH$_2$Br | (A) | 2 | —$^{(e)}$ | 80:20 |

TABLE 2-continued

Compounds of formula:

$$\underset{R^2}{\overset{R^1}{\diagdown}}C=CH-\underset{|}{\overset{R^3}{C}}=\underset{|}{\overset{R^4}{C}}-CH_2Z$$

| Compound No. (Mixture No.) | Formula[a] | Starting Product(s) (see Table 1) | Boiling Point of collected fraction (°C./mmHg) | Positional Isomers ratio[b] (A/B) |
|---|---|---|---|---|
| | $CF_3-\underset{\underset{Br}{\vert}}{C}=CH-CH=C(CH_3)-CH_2Br$ | (B) | | |
| 23 | $CCl_2=CH-CH=C(CH_3)-CH_2Br$ | —[f] | 93–95/2 | |
| 24 | $(CH_3)_2C=CH-CH=C(CH_3)-CH_2Br$ | —[g] | 85–86/12 | |

Notes to Table 2
[a] Mixture of cis and trans isomers
[b] Approximate ratio determined by NMR spectroscopy
[c] The preparation is described in Example 4
[d] Compounds of mixture No. 20 decompose when distilled, Mass-spectroscopic data (M⁺/e) 248 (10%), 246 (10%), 167 (80%), 147 (56%), 127 (60%), 69 (30%), 53 (100%)
[e] Compounds of mixture No. 21 decompose when distilled Mass-spectroscopic data (M⁺/e) 310 (8%), 308 (16%), 306 (8%), 229 (50%), 227 (50%), 148 (45%), 147 (90%), 127 (100%).
[f] The preparation is described in Example 5.
[g] The preparation is described in Example 6.

EXAMPLE 8

Preparation of 4-[(5,5-dichloro-3-methyl-penta-2,4-dien-1-yl)-thio]-2-nitro-aniline (A) and of 4-[(5,5-dichloro-2-methyl-penta-2,4-dien-1-yl)-thio]-2-nitro-aniline (B)

[Reaction III, X=S, R⁵=H]

A solution of 10 g (51.2 m.moles) of 2-nitro-4-thiocyano-aniline in 25 ml of dimethylformamide (DMF) was added to a solution of 2.26 g (51 m.moles) of sodium-boron-hydride in 25 ml of dimethylformamide. The reaction mixture was maintained under stirring at room temperature for 1 hour, whereupon 60 m.moles of the mixture of the products obtained as described in Example 3 were added. The reaction mixture was heated to 100° C. for 1 hour, then it was allowed to cool down and was poured into 200 ml of H₂O. It was extracted with chloroform (3×100 ml). The organic extracts were reunited, anhydrified with anhydrous Na₂SO₄, and the solvent was removed under vacuum.

A crude product (11.9 g) was obtained, which consisted of compounds A and B in a ratio of about 55:45 (NMR) and resulted sufficiently pure for the successive step (Example 9).

EXAMPLE 9

Preparation of 4-[(5,5-dichloro-3-methyl-penta-2,4-dien-1-yl)thio]-1,2-phenylenediamine (A) and of 4-[(5,5-dichloro-2-methyl-penta-2,4-dien-1-yl)-thio]-1,2-phenylendiamine (B)

[Reaction VI]

11.7 g of the crude product obtained as described in example 8 were added to a mixture of 200 ml of H₂O and 200 ml of CH₃OH containing 45 g of Na₂S₂O₄.

The reaction mixture was heated to 80° C. for 15 minutes, whereupon the inorganic salts were filtered and a methanol portion was removed under vacuum.

After extraction with chloroform (3×100 ml), the organic phases were reunited, anhydrified with anhydrous Na₂SO₄, and the solvent was removed, so obtaining a brown viscous oil composed by products A and B in a ratio of about 55:45 (NMR).

EXAMPLE 10

Preparation of 5(6)-[(5,5-dichloro-3-methyl-penta-2,4-dien-1-yl)-thio]-benzimidazole-2-methylcarbamate (A) and of 5(6)[(5,5-dichloro-2-methyl-penta-2,4-dien-1-yl)-thio]-benzimidazole-2-methylcarbamate (2)

[Reaction VII]

8.5 g (29.4 m.moles) of the raw oil obtained as described in Example 9 were dissolved in a mixture of 35 ml of H₂O, 35 ml of ethanol, 2 ml of acetic acid and 6.05 g (29.4 m.moles) of 1,3-bis-methoxycarbonyl-S-methyl-isothiourea. The reaction mixture was heated at reflux for 2 hours. A solid formed, which was separated by filtration and was re-crystallized by methanol and chloroform (1:1). 7 g of a mixture of compounds A and B in a ratio of about 55:45 (NMR) (melting point 169°–170° C. with decomposition) were obtained.

EXAMPLE 11

Preparation of 5(6)-[(5,5-dichloro-3-methyl-penta-2,4-dien-1-yl)-sulphinyl]-benzimidazole-2-methylcarbamate (A) and of 5(6)-[(5,5-dichloro-2-methyl-penta-2,4-dien-1-yl)-sulphinyl]-benzimidazole-2-methylcarbamate (B)

[Reaction VIII]

10.1 m.moles of 3-chloro-perbenzoic acid were rapidly added, under intense stirring, to a solution of 4 g (10.7 m.moles) of the mixture of products obtained as described in example 10, in 400 ml of chloroform, 200 ml of ethanol and 1.5 ml of acetic acid. The reaction mixture was left at room temperature for 1 hour, then it was treated with an aqueous solution of NaHCO₃ and successively with water until a neutral pH was attained. The organic solution was anhydrified with anhydrous Na₂SO₄ and the solvent was evaporated under vacuum. The residual oil was washed with methanol and ethyl ether, and the resulting solid was re-crystallized by methanol, so obtaining 3.5 g of a mixture of products A and B in a ratio of about 55:45 (melting point=134°–135° C. with decomposition).

EXAMPLE 12

Preparation of
4-[(5,6,6,6-tetrafluoro-3-methyl-hexa-2,4-dien-1-yl)-thio]-2-nitro-aniline (A) and of
4-[(5,6,6,6-tetrafluoro-2-methyl-hexa-2,4-dien-1-yl)-thio]-2-nitro-aniline (B)

[Reaction IV and V]

A solution of 10.5 g of NaBH$_4$ in 15 ml of dimethylformamide was added, at room temperature, to a solution of 5 g of 2-nitro-4-thio-cyano-aniline (25.6 m.moles) in 15 ml of dimethylformamide. The reaction mixture was maintained under stirring at room temperature for 1 hour, whereupon 8.85 g (27 m.moles) of mixture No. 2 (see Table 1), were added. The reaction mixture was heated to 100° C. for 1 hour. After cooling 4.9 ml (35 m.moles) of triethylamine were added, then it was heated to 100° C. for 2 hours. The mixture was cooled and then diluted with 300 ml of H$_2$O and extracted with chloroform (4×100 ml). The organic phase was anhydrified with anhydrous Na$_2$SO$_4$, concentrated under vacuum and was chromatographied on silica gel (eluent: ethyl ether-petroleum ether 1:1). 5.8 g (red oil) of a mixture of compounds A and B in ratio of about 1:1 (NMR) were obtained.

EXAMPLE 13

Preparation of
4-[(5,6,6,6-tetrafluoro-3-methyl-hexa-2,4-dien-1-yl)-thio]-1,2-phenylenediamine (A) and of
4-[(5,6,6,6-tetrafluoro-2-methyl-hexa-2,4-dien-1-yl)-thio]-1,2-phenylenediamine(B)

[Reaction VI]

Starting from 5.7 g of the mixture of the 2-nitro-anilines obtained as described in Example 12 and operating as described in Example 9, 4.6 g of an intensely colored oil, consisting of a mixture of compounds A and B in a ratio of about 1:1 (NMR), were obtained.

EXAMPLE 14

Preparation of
5(6)-[(5,6,6,6-tetrafluoro-3-methyl-hexa-2,4-dien-1-yl)-thio]-benzimidazole-2-methylcarbamate (A) and of
5(6)-[(5,6,6,6-tetrafluoro-2-methyl-hexa-2,4-dien-1-yl)-thio]-benzimidazole-2-methylcarbamate (B)

[Reaction VII]

4.6 g (1.5 m.moles) of the mixture of compounds obtained as described in Example 13 were dissolved in a mixture of 20 ml of H$_2$O, 20 ml of ethanol and 0.5 ml of acetic acid containing 3.1 g (1.5 m.moles) of 1,3-bis-methoxycarbonyl-S-methyl-isothiourea. The reaction mixture was heated at reflux for 2 hours, then it was allowed to cool. A solid formed, which was separated by filtration and crystallized by methanol-chloroform (1:1), so obtaining 3.7 g of a mixture of compounds A and B in a ratio of about 1:1 (melting point: 167°–170° C.).

EXAMPLE 15

Preparation of
5(6)-[(5,6,6,6-tetrafluoro-3-methyl-hexa-2,4-dien-1-yl)-sulphinyl]-benzimidazole-2-methylcarbamate (A) and of
5(6)-[(5,6,6,6-tetrafluoro-3-methyl-hexa-2,4-dien-1-yl)-sulphinyl]-benzimidazole-2-methylcarbamate (B)

[Reaction VIII]

Starting from 1.3 g (3.34 m.moles) of the mixture of benzimidazole carbamates obtained as described in Example 14 and operating as described in Example 11, it was possible to obtain 0.95 g of a mixture of compounds A and B in a ratio of about 1:1 (NMR) (melting point: 147°–149° C.).

EXAMPLE 16

Preparation of
4-[(5,5-dichloro-3-methyl-penta-2,4-dien-1-yl)-oxy]-2-nitro-aniline (A) and of
4-[(5,5-dichloro-2-methyl-penta-2,4-dien-1-yl)-oxy]-2-nitro-aniline (B)

[Reaction III, X=O, R$^5$=CH$_3$CO]

A mixture of 10.2 g (52 m.moles) of 3-nitro-4-acetamino-phenol, 20 g of Na$_2$CO$_3$, 11.12 g (60 m.moles) of the mixture No. 18 (see Table 2) and 60 ml of acetone was heated at reflux for 48 hours. The reaction mixture was then allowed to cool, the inorganic salts were filtered and a part of the solvent was removed. The resulting crude product was subjected to chromatography on silica gel (eluent: ethyl ether-petroleum ether 1:1); 7.8 g of a brown crystalline solid consisting of a mixture of compounds A and B in a ratio of about 3:2 (NMR) were obtained.

EXAMPLE 17

Preparation of
4-[(5,5-dichloro-3-methyl-penta-2,4-dien-1-yl)-oxy]-1,2-phenylenediamine (A) and of
4-[(5,5-dichloro-2-methyl-penta-2,4-dien-1-yl)-oxy]-1,2-phenylenediamine (B)

[Reaction VI]

Starting from 7.5 g of the mixture of compounds obtained as described in Example 16 and operating as illustrated in Example 9 it was possible to obtain 6.2 g of a thick brown oil consisting of a mixture of compounds A and B in a ratio of about 3:2.

EXAMPLE 18

Preparation of
5(6)-[(5,5-dichloro-3-methyl-penta-2,4-dien-1-yl)-oxy]-benzimidazole-2-methylcarbamate (A) and of
5(6)-[(5,5-dichloro-2-methyl-penta-2,4-dien-1-yl)-oxy]-benzimidazole-2-methyl-carbamate (B)

[Reaction VI]

4.6 g of 1,3-bis-methoxycarbonyl-S-methyl-isothiourea were added to a solution of 6.2 g (22.7 m.moles) of the mixture of products obtained as described in Example 17, in 30 ml of H$_2$O, 30 ml of ethanol and 0.8 ml of acetic acid. The reaction mixture was heated at reflux for 2 hours, whereupon it was allowed to cool. A solid formed, which was filtered and crystallized by methanolchloroform, so obtaining 5.6 g of a mixture of compounds A and B in a ratio of about 3:2 (NMR) (melting point: 183°-185° C.).

EXAMPLE 19

On the following Table 3 benzimidazole-carbamates of general formula I are reported, together with their characteristics and the synthesis procedure.

TABLE 3

Compounds of formula $$R^1R^2C=CH-C(R^3)=C(R^4)-CH_2-X-\text{benzimidazole}-NH-COOCH_3$$

(BIAC = benzimidazole-NH—COOCH$_3$)

| Sample No. | Formula[a] | Starting[b] Product(s) | Procedure of examples no | Melting Point[c] (°C.) | Positional Isomers Ratio[d] (A/B) | Analysis[e] |
|---|---|---|---|---|---|---|
| 25 | CCl$_2$=CH—CH=CH—CH$_2$—S—BIAC | 19 | 8-10 | 188-192 | | NMR,MS,EA |
| 26 | CCl$_2$=CH—CH=CH—CH$_2$—SO—BIAC | 25 | 11 | 190(dec) | | NMR |
| 27 | CCl$_2$=CH—CH=CH—CH$_2$—SO$_2$—BIAC | 25 | 11[f] | 235-40 | | NMR,EA |
| 28 | CCl$_2$=CH—C(CH$_3$)=CH—CH$_2$—S—BIAC(A) CCl$_2$=CH—CH=C(CH$_3$)—CH$_2$—S—BIAC(B) | 18 | 8-10 | 169-70 | 55:45 | NMR,EA |
| 29 | CCl$_2$=CH—C(CH$_3$)=CH—CH$_2$—SO—BIAC(A) CCl$_2$=CH—CH=C(CH$_3$)—CH$_2$—SO—BIAC(B) | 28 | 11 | 134-5 | 55:45 | NMR |
| 30 | CBr$_2$=CH—C(CH$_3$)=CH—CH$_2$—S—BIAC(A) CBr$_2$=CH—CH=C(CH$_3$)—CH$_2$—S—BIAC(B) | 17 | 12-14 | n.d. | 55:45 | NMR,EA,MS |
| 31 | CBr$_2$=CH—C(CH$_3$)=CH—CH$_2$—SO—BIAC(A) CBr$_2$=CH—CH=C(CH$_3$)—CH$_2$—SO—BIAC(B) | 30 | 11 | n.d. | 55:45 | NMR,IR |
| 32 | CF$_2$=CH—C(CH$_3$)=CH—CH$_2$—S—BIAC(A) CF$_2$=CH—CH=C(CH$_3$)—CH$_2$—S—BIAC(B) | 5 | 12-14 | n.d. | 55:45 | NMR,MS |
| 33 | CF$_2$=CH—C(CH$_3$)=CH—CH$_2$—SO—BIAC(A) CF$_2$=CH—CH=C(CH$_3$)—CH$_2$—SO—BIAC(B) | 32 | 11 | n.d. | 60:40 | NMR,IR,MS |
| 34 | CF$_3$—CF=CH—C(CH$_3$)=CH—CH$_2$—S—BIAC(A) CF$_3$—CF=CH—CH=C(CH$_3$)—CH$_2$—S—BIAC(B) | 3 | 12-14 | 167-70 | 50:50 | NMR,MS |
| 35 | CF$_3$—CF=CH—C(CH$_3$)=CH—CH$_2$—SO—BIAC(A) CF$_3$—CF=CH—CH=C(CH$_3$)—CH$_2$—SO—BIAC(B) | 34 | 15 (11) | 147-9 | 50:50 | NMR,MS |
| 36 | CF$_3$—CH=CH—C(CH$_3$)=CH—CH$_2$—S—BIAC(A) CF$_3$—CH=CH—CH=C(CH$_3$)—CH$_2$—S—BIAC(B) | 8 (B) | 12-14 | 158-62 | 65:35 | NMR,IR,EA |
| 37 | CF$_3$—CH=CH—C(CH$_3$)=CH—CH$_2$—SO—BIAC(A) CF$_3$—CH=CH—CH=C(CH$_3$)—CH$_2$—SO—BIAC(B) | 36 | 11 | 165-73 | 65:35 | NMR,IR,EA |
| 38 | CCl$_2$=CH—C(CH$_3$)=CH—CH$_2$—O—BIAC(A) CCl$_2$=CH—CH=C(CH$_3$)—CH$_2$—O—BIAC(B) | 18 | 16-18 | 183-5 | 60:40 | NMR |
| 39 | CH$_3$—CCl=CH—C(CH$_3$)=CH—CH$_2$—S—BIAC(A) CH$_3$—CCl=CH—CH=C(CH$_3$)—CH$_2$—S—BIAC(B) | 20 | 8-10 | 154-5 | 85:15 | NMR |
| 40 | CH$_3$—CCl=CH—C(CH$_3$)=CH—CH$_2$—SO—BIAC(A) CH$_3$—CCl=CH—CH=C(CH$_3$)—CH$_2$—SO—BIAC(B) | 39 | 11 | 138-44 | 85:15 | NMR |
| 41 | CH$_3$—CCl=CH—C(CH$_3$)=CH—CH$_2$—SO$_2$—BIAC(A) CH$_3$—CCl=CH—CH=C(CH$_3$)—CH$_2$—SO$_2$—BIAC(B) | 39 | 11[f] | 178-84 | 85:15 | NMR |
| 42 | (CH$_3$)$_2$C=CH—CH=C(CH$_3$)—CH$_2$—S—BIAC | 24 | 6,8-10 | 233-5 | | NMR,MS |
| 43 | (CH$_3$)$_2$C=CH—CH=C(CH$_3$)—CH$_2$—SO—BIAC | 42 | 11 | 242-5 | | NMR,IR,EA |
| 44 | CH$_3$—CCl=CH—CH=CH—CH$_2$—S—BIAC | 14 | 8-10 | 181-2 | | NMR |
| 45 | CH$_3$—CCl=CH—CH=CH—CH$_2$—SO—BIAC | 44 | 11 | 140-3(dec) | | NMR |
| 46 | CH$_3$—CCl=CH—CH=CH—CH$_2$—SO—BIAC | 44 | 11[f] | 202(dec) | | NMR |
| 47 | CCl$_2$=CH—C(CH$_3$)=CH—CH$_2$—SO$_2$—BIAC(A) CCl$_2$=CH—CH=C(CH$_3$)—CH$_2$—SO$_2$—BIAC(B) | 28/3[g] | 11[f] | 195-200 | 70:30 | NMR |

TABLE 3-continued

Compounds of formula

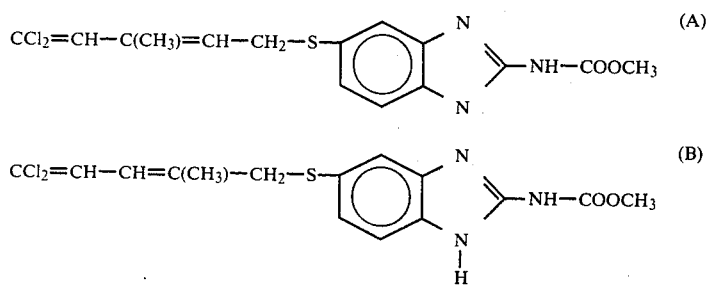

| Sample No. | Formula[a] | Starting[b] Product(s) | Procedure of examples no | Melting Point[c] (°C.) | Positional Isomers Ratio[d] (A/B) | Analysis[e] |
|---|---|---|---|---|---|---|
| 48 | $CCl_2=CH-CH=C(CH_3)-CH_2-S-BIAC$ | 23 | 5,8-10 | 177-80 | | NMR,EA |

EXAMPLE 20

Compounds of general formula I were tested for anthelmintic activity according to the procedure described at page 11.

Samples Nos. 25, 26, 28, 29, 30, 31, 32, 33, 34, 35, 36, 37, 39, 40, 44, 45 and 47 (see Table 3) tested against Gut-nematodes in infested sheep, proved to be completely effective (90-100% reduction of infestation) at the dose of 5 mg/Kg of body weight. Samples Nos. 28, 29, 35 and 40 tested against Flukes (Fasciola) in infested sheep, proved to be completely effective (90-100% reduction of infestation) at the dose of 5 mg/Kg of body weight. Samples Nos. 32 and 44 tested against Lungworms (Dictyocaulus) in infested sheep, proved to be completely effective (90-100% reduction of infestation) at the dose of 5 and 2.5 mg/Kg of body weight respectively.

EXAMPLE 21

Anthelmintic Activity of Positional Isomers Mixtures Having Different Isomeric Composition Sample No. 28 (see Table 3) is a mixture of compound A and compound B in the ratio A/B=55:45

$CCl_2=CH-C(CH_3)=CH-CH_2-S-$ [benzimidazole]$-NH-COOCH_3$ (A)

$CCl_2=CH-CH=C(CH_3)-CH_2-S-$ [benzimidazole]$-NH-COOCH_3$ (B)

Sample No. 48 (see Table 3) is compound B (100%).
A mixture consisting of compounds a and b in the ratio a/b==75:25 (NMR)

$CCl_2=CH-C(CH_3)=CH-CH_2Cl$ (a)

$CCl_2=CH-CH=C(CH_3)-CH_2Cl$ (b)

was distilled at reduced pressure.

The following fractions were collected:

| Fraction No. | B.p. (°C./mmHg) | Composition a/b (NMR) |
|---|---|---|
| 1 | 50-54/0.5 | 90:10 |
| 2 | 54-57/0.5 | 80:20 |
| 3 | 57/0.5 | 70:30 |

From fractions B 1 and 3 independently and by operating as described in Examples 8-10, the corresponding benzimidazole-carbamate derivatives (Samples 28/1 and 28/3) were prepared.

| | | | |
|---|---|---|---|
| Sample 28/1 | A/B = 90:10 (NMR) | m.p. = 163-5° C. | |
| Sample 28/3 | A/B = 70:30 (NMR) | m.p. = 160-5° C. | |

Samples 28, 28/1, 28/3 and 48 were separately tested for anthelmintic activity against Gut-nematodes in infested sheeps.

The obtained activity data are reported on the following Table 4 and are expressed according to the following scale of values:

| | |
|---|---|
| 0 | 0-10% reduction of infestation |
| 1 | 11-25% reduction |
| 2 | 26-60% reduction |
| 3 | 61-90% reduction |
| 4 | 91-100% reduction |

TABLE 4

| Sample No. | Compositions of Sample (%) | dose (mg/Kg) | Activity |
|---|---|---|---|
| 28 | A = 55, B = 45 | 5 | 4 |
| 28/1 | A = 90, B = 10 | 5 | 4 |
| 28/3 | A = 70, B = 30 | 5 | 4 |
| 48 | A = 0, B = 100 | 2.5 | 3 |

EXAMPLE 22

Activity Against *Brugia pahangi* (Filarioidea)

In Vivo *Brugia pahangi* Adult Worm Transplant Screen

Yound male adult jirds were infested with large numbers of infected larvae by the intraperitoneal route. 60 days later adult worms were recovered, washed, sexed and counted into groups of 10 female and 5 male. These were then transplanted into the peritoneal cavities of naive (normal) jirds. Following a recovery period, the compound to be tested was administered at 100 mg/kg for 5 consecutive days by subcutaneous injection. The compound was formulated in 1% Tween 80.

Each compound was tested in two animals. If the drug was inactive a worm recovery of 85–90% was expected; this was then considered to be a "pseudo-control". In this way "control" groups of 20 or more animals can be used, against which active compounds were compared. The selection of pseudo-controls is thus subjective but the hypothesis that a compound is inactive was tested by the "F test". If the variances of the pseudo-controls were homogeneous, then the active compounds were tested against this group by the "student t" test.

At autopsy (32 days after administration of the final dose of compound), the peritoneal fluid was also examined for the presence of microfilariae. When these were absent, present in only small numbers, or abnormal, the adult worms were examined to determine if the compound had effected embryogenesis and/or spermetogenesis.

Reference to the "F test" and "student t" test may be found in Snedecor and Cochran, Statistical Methods, published by Iowa State University Press at pages 258–268.

The following scores were allocated according to the percentage worm reduction observed:

| Percentage worm reduction | Score |
|---|---|
| 0–10% | 0 |
| 11–25% | 1 |
| 26–60% | 2 |
| 61–90% | 3 |
| 91–100% | 4 |

Samples Nos. 25, 29, 35, 44 and 45 (see Table 3) tested against *Brugia pahangi* according to the above reported procedure proved to be completely effective (91–100% reduction of infestation, score 4).

What we claim is:

1. A benzimidazole-carbamate substituted in position 5(6) and of the formula:

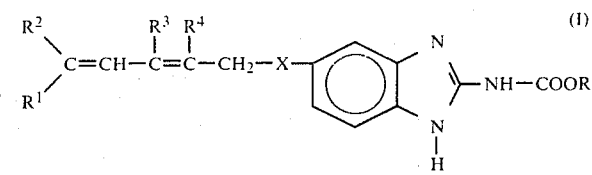

wherein:
R = $C_1$-$C_4$ alkyl,
$R^1$ and $R^2$ (like or unlike each other) = H, halogen, methyl optionally substituted by one or more halogen atoms,
$R^3$ and $R^4$ (like or unlike each other) = H, Cl, $CH_3$,
X = O, S, SO, $SO_2$, and mixed positional isomers thereof.

2. A benzimidazole-carbamate according to claim 1 in which $R^1$ is halogen, $CH_3$, $CF_3$ and $R^2$ is H, halogen, $CH_3$; $R^3$ and $R^4$ = H, $CH_3$, in which at least one is H; R and X have the meanings specified in claim 1, and mixed positional isomers thereof.

3. A benzimidazole-carbamate according to claim 2, in which R = $CH_3$ and $R^1$, $R^2$, $R^3$, $R^4$ and X have the meanings specified in claim 2, and mixed positional isomers thereof.

4. A benzimidazole-carbamate according to claim 3 in which $R^1$ and $R^2$ = halogen, and mixed positional isomers thereof.

5. A benzimidazole-carbamate according to claim 4 in which $R^1$ = $R^2$ = Cl, $R^3$ = $R^4$ = H and X = S, and mixed positional isomers thereof.

6. A benzimidazole-carbamate according to claim 4 in which $R^1$ = $R^2$ = Cl, $R^3$ = $R^4$ = H and X = SO, and mixed positional isomers thereof.

7. A benzimidazole-carbamate according to claim 4 in which $R^1$ = $R^2$ = Cl, $R^3$ = $R^4$ = H and X = SO, and mixed positional isomers thereof.

8. A benzimidazole-carbamate according to claim 4 in which $R^1$ = $R^2$ = Cl, $R^3$ and $R^4$ (different from each other) = H, $CH_3$ and X = O, and mixed positional isomers thereof.

9. A benzimidazole-carbamate according to claim 4 in which $R^1$ = $R^2$ = Cl, $R^3$ and $R^4$ (different from each other) = H, $CH_3$ and X = S, and mixed positional isomers thereof.

10. A benzimidazole-carbamate according to claim 4 in which $R^1$ = $R^2$ = Cl, $R^3$ and $R^4$ (different from each other) = H, $CH_3$, and X = SO, and mixed positional isomers thereof.

11. A benzimidazole-carbamate according to claim 4 in which $R^1$ = $R^2$ = Cl, $R^3$ and $R^4$ (different from each other) = H, $CH_3$ and X = $SO_2$, and mixed positional isomers thereof.

12. A benzimidazole-carbamate according to claim 4 in which $R^1$ = $R^2$ = Br, $R^3$ and $R^4$ (different from each other) = H, $CH_3$ and X = S, and mixed positional isomers thereof.

13. A benzimidazole-carbamate according to claim 4 in which $R^1$ = $R^2$ = Br, $R^3$ and $R^4$ (different from each other) = H, $CH_3$ and X = SO, and mixed positional isomers thereof.

14. A benzimidazole-carbamate according to claim 4 in which $R^1$ = $R^2$ = F, $R^3$ and $R^4$ (different from each other) = H, $CH_3$ and X = S, and mixed positional isomers thereof.

15. A benzimidazole-carbamate according to claim 4 in which $R^1$ = $R^2$ = F, $R^3$ and $R^4$ (different from each other) = H, CH$_3$ and X = SO, and mixed positional isomers thereof.

16. A benzimidazole-carbamate according to claim 3 in which R$^1$ = CF$_3$, R$^2$ = H, halogen and X has the meanings specified in claim 1, and mixed positional isomers thereof.

17. A benzimidazole-carbamate according to claim 16 in which R$^1$ = CF$_3$, R$^2$ = H, R$^3$ and R$^4$ (different from each other) = H, CH$_3$ and X = S, and mixed positional isomers thereof.

18. A benzimidazole-carbamate according to claim 16 in which R$^1$ = CF$_3$, R$^2$ = H, R$^3$ and R$^4$ (different from each other) = H, CH$_3$ and X = SO, and mixed positional isomers thereof.

19. A benzimidazole-carbamate according to claim 16 in which R$^1$ = CF$_3$, R$^2$ = F, R$^3$ and R$^4$ (different from each other) = H, CH$_3$ and X = S, and mixed positional isomers thereof.

20. A benzimidazole-carbamate according to claim 16 in which R$^1$ = CF$_3$, R$^2$ = F, R$^3$ and R$^4$ (different from each other) = H, CH$_3$ and X = SO, and mixed positional isomers thereof.

21. A benzimidazole-carbamate according to claim 3 in which R$^1$ = CH$_3$, R$^2$ = H, halogen and X has the meanings specified in claim 1, and mixed positional isomers thereof.

22. A benzimidazole-carbamate according to claim 21 in which R$^1$ = CH$_3$, R$^2$ = Cl, R$^3$ = R$^4$ = H and X = S, and mixed positional isomers thereof.

23. A benzimidazole-carbamate according to claim 21 in which R$^1$ = CH$_3$, R$^2$ = Cl, R$^3$ = R$^4$ = H and X = SO, and mixed positional isomers thereof.

24. A benzimidazole-carbamate according to claim 21 in which R$^1$ = CH$_3$, R$^2$ = Cl, R$^3$ = R$^4$ = H and X = SO$_2$, and mixed positional isomers thereof.

25. A benzimidazole-carbamate according to claim 21 in which R$^1$ = CH$_3$, R$^2$ = Cl, R$^3$ and R$^4$ (different from each other) = H, CH$_3$ and X = S, and mixed positional isomers thereof.

26. A benzimidazole-carbamate according to claim 21 in which R$^1$ = CH$_3$, R$^2$ = Cl, R$^3$ and R$^4$ (different from each other) = H, CH$_3$ and X = SO, and mixed positional isomers thereof.

27. A benzimidazole-carbamate according to claim 21 in which R$^1$ = CH$_3$, R$^2$ = Cl, R$^3$ and R$^4$ (different from each other) = H, CH$_3$ and X = SO$_2$, and mixed positional isomers thereof.

28. A benzimidazole-carbamate according to claim 3 in which R$^1$ = R$^2$ = CH$_3$ and X has the meanings specified in claim 1, and mixed positional isomers thereof.

29. A benzimidazole-carbamate according to claim 28 in which R$^1$ = R$^2$ = R$^4$ = CH$_3$, R$^3$ = H, and X = S, and mixed positional isomers thereof.

30. A benzimidazole-carbamate according to claim 28 in which R$^1$ = R$^2$ = R$^4$ = CH$_3$, R$^3$ = H and X = SO, and mixed positional isomers thereof.

31. Method for fighting infestations due to helminthes in domestic and breeding animals, characterized in that an effective amount of a benzimidazole-carbamate of claim 1, or of a mixture of positional isomers thereof, either as such or in the form of a suitable composition, is administered to the animals to be treated.

32. Method according to claim 31, characterized in that the helminthes to be fought belong to the order of Filarioidea.

33. The method according to claim 31, characterized in that a benzimidazole-carbamate or mixture of positional isomers of claim 1 is administered orally to the infested animals in the form of a suitable composition or admixed with the food.

34. The method according to claim 31, characterized in that a benzimidazole-carbamate or mixture of positional isomers of claim 1 is administered by injection of the infested animals in the form of a suitable, liquid injectable composition.

35. The method according to claim 31, characterized in that a benzimidazole-carbamate or mixture of positional isomers of claim 1 is administered to the infested animals in the form of a suitable composition absorbable through the skin of the animals.

36. The method of claim 31 characterized in that the anthelmentic agent is a benzimidazole carbamate or isomer mixture of claim 4.

37. The method of claim 31 characterized in that the anthelmintic agent is a benzimidazole carbamate or isomer mixture of claim 16.

38. The method of claim 31 characterized in that the anthelmintic agent is a benzimidazole carbamate or isomer mixture of claim 21.

39. The method of claim 31 characterized in that the anthelmintic agent is a benzimidazole carbamate or isomer mixture of claim 28.

40. An anthelmintic composition for veterinary use comprising as active ingredient an effective amount of a benzimidazole-carbamate or isomer mixture of claim 1 and a suitable non-toxic carrier.

41. An anthelmintic composition according to claim 40, characterized in that the active ingredient is a benzimidazole-carbamate or isomer mixture of claim 4.

42. An anthelmintic composition according to claim 40, characterized in that the active ingredient is a benzimidazole-carbamate or isomer mixture of claim 16.

43. An anthelmintic composition according to claim 40, characterized in that the active ingredient is a benzimidazole-carbamate or isomer mixture of claim 21.

44. An anthelmintic composition according to claim 40, characterized in that the active ingredient is a benzimidazole-carbamate or isomer mixture of claim 28.

* * * * *

UNITED STATES PATENT AND TRADEMARK OFFICE
CERTIFICATE OF CORRECTION

PATENT NO. : 4,299,837

DATED : November 10, 1981

INVENTOR(S) : Paolo PICCARDI et al

Page 1 of 3

It is certified that error appears in the above—identified patent and that said Letters Patent is hereby corrected as shown below:

Table 3, Cols. 15 - 16, Sample No. 36, under the column heading "Starting Product(s)",

- - - delete "(B)" under the numeral "8"; - - -

Table 3, Cols. 15 - 16, Sample No. 46, the correct formula is

- - - $CH_3-CCl=CH-CH=CH-CH_2-SO_2-BIAC-$; - - -

After Table 3, in Col. 17, before "EXAMPLE 20", add the following footnotes: - - - Notes to Table 3

(a) Mixture of cis and trans isomers (b) Products 1-17 and 18-24 are reported on Table 1 and Table 2 respectively (c) Melting points have not been corrected dec. = decomposition, n.d. = not determined (d) Approximate ratio determined by NMR spectroscopy

UNITED STATES PATENT AND TRADEMARK OFFICE
CERTIFICATE OF CORRECTION

PATENT NO. : 4,299,837
DATED : November 10, 1981
INVENTOR(S) : Paolo PICCARDI et al It is certified that error appears in the above—identified patent and that said Letters Patent is hereby corrected as shown below:

(e) Structures confirmed by the performed analysis

NMR = Nuclear Magnetic Resonance spectroscopy

IR = Infra-red spectroscopy

MS = Mass spectroscopy

EA = Elemental analysis (f) Prepared by a procedure analogous to the one described in Example 11, by using two equivalents of 3-chloro-perbenzoic acid.

(g) Mixture 28/3 is described in Example No. 21

- - -;

Col. 17, formula (A) of Example 21 should read as follows:

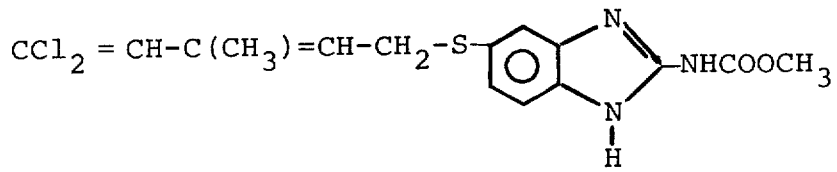

UNITED STATES PATENT AND TRADEMARK OFFICE
CERTIFICATE OF CORRECTION

PATENT NO. : 4,299,837
DATED : November 10, 1981
INVENTOR(S) : Paolo Piccardi et al.

It is certified that error appears in the above—identified patent and that said Letters Patent is hereby corrected as shown below:

Column 17, Example 21, the third line after formula (B) should read -- ratio a/b = 75:25 (NMR). --.

Signed and Sealed this

Thirteenth Day of April 1982

|SEAL|

Attest:

GERALD J. MOSSINGHOFF

Attesting Officer    Commissioner of Patents and Trademarks